US011951026B2

(12) United States Patent
Clinger et al.

(10) Patent No.: US 11,951,026 B2
(45) Date of Patent: Apr. 9, 2024

(54) IMPLANTABLE MEDICAL DEVICE DETACHMENT SYSTEM WITH FLEXIBLE BRAID SECTION

(71) Applicant: DePuy Synthes Products, Inc., Raynham, MA (US)

(72) Inventors: Melissa Clinger, Raynham, MA (US); Kirk Johnson, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 235 days.

(21) Appl. No.: 16/916,565

(22) Filed: Jun. 30, 2020

(65) Prior Publication Data

US 2021/0401601 A1   Dec. 30, 2021

(51) Int. Cl.
*A61B 17/12* (2006.01)
*A61F 2/95* (2013.01)
*A61F 2/962* (2013.01)

(52) U.S. Cl.
CPC ....... *A61F 2/962* (2013.01); *A61F 2002/9511* (2013.01); *A61F 2002/9534* (2013.01)

(58) Field of Classification Search
CPC .............. A61F 2/962; A61F 2002/9511; A61F 2002/9534; A61B 17/12014; A61B 17/12019; A61B 17/1214–17/12154; A61B 2017/1205–2017/12095
See application file for complete search history.

(56) References Cited

U.S. PATENT DOCUMENTS

| 2,220,203 A | 2/1939 | Branin |
| 3,429,408 A | 2/1969 | Maker |
| 4,858,810 A | 8/1989 | Intlekofer et al. |
| 5,108,407 A | 4/1992 | Geremia et al. |
| 5,122,136 A | 6/1992 | Guglielmi et al. |
| 5,234,437 A | 8/1993 | Sepetka |
| 5,250,071 A | 10/1993 | Palermo |
| 5,263,964 A | 11/1993 | Purdy |
| 5,334,210 A | 8/1994 | Gianturco |

(Continued)

FOREIGN PATENT DOCUMENTS

| CN | 104203341 A | 12/2014 |
| CN | 106456422 A | 2/2017 |

(Continued)

OTHER PUBLICATIONS

Extended European Search Report issued in European Patent Application No. 21 18 2230 dated Nov. 25, 2021.

*Primary Examiner* — Kathleen S Holwerda
(74) *Attorney, Agent, or Firm* — TROUTMAN PEPPER HAMILTON SANDERS LLP (57) ABSTRACT

The disclosed technology includes a detachment system for delivering an implantable medical device to a target location of a body vessel including a proximal delivery tube, a distal delivery tube, and a braid segment disposed between. The distal tube includes a proximal end, a distal end, and a compressible portion of the tube itself, between the proximal and distal ends which is axially movable from a compressed to an elongated condition. The proximal tube has a proximal end and a distal end. The braid segment is formed from a plurality of wires. An engagement system engages and deploys the implantable medical device engaged at the distal end of the distal tube.

18 Claims, 8 Drawing Sheets

(56) References Cited

U.S. PATENT DOCUMENTS

| | | | |
|---|---|---|---|
| 5,350,397 A | 9/1994 | Palermo et al. | |
| 5,382,259 A | 1/1995 | Phelps et al. | |
| 5,392,791 A | 2/1995 | Nyman | |
| 5,484,409 A | 1/1996 | Atkinson et al. | |
| 5,569,221 A | 10/1996 | Houser et al. | |
| 5,899,935 A | 5/1999 | Ding | |
| 5,925,059 A | 7/1999 | Palermo et al. | |
| 6,113,622 A | 9/2000 | Hieshima | |
| 6,203,547 B1 | 3/2001 | Nguyen et al. | |
| 6,391,037 B1 | 5/2002 | Greenhalgh | |
| 6,454,780 B1 | 9/2002 | Wallace | |
| 6,506,204 B2 | 1/2003 | Mazzocchi | |
| 6,561,988 B1 | 5/2003 | Turturro et al. | |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,384,407 B2 * | 6/2008 | Rodriguez | A61N 7/00 604/22 |
| 7,708,754 B2 | 5/2010 | Balgobin et al. | |
| 7,708,755 B2 | 5/2010 | Davis, III et al. | |
| 7,799,052 B2 | 9/2010 | Balgobin et al. | |
| 7,811,305 B2 | 10/2010 | Balgobin et al. | |
| 7,819,891 B2 | 10/2010 | Balgobin et al. | |
| 7,819,892 B2 | 10/2010 | Balgobin et al. | |
| 7,901,444 B2 | 3/2011 | Slazas | |
| 7,985,238 B2 | 7/2011 | Balgobin et al. | |
| 8,062,325 B2 | 11/2011 | Mitelberg et al. | |
| 8,333,796 B2 | 12/2012 | Tompkins et al. | |
| 8,926,650 B2 | 1/2015 | Que et al. | |
| 8,956,381 B2 | 2/2015 | Que et al. | |
| 9,155,540 B2 | 10/2015 | Lorenzo | |
| 9,232,992 B2 | 1/2016 | Heidner | |
| 9,314,326 B2 | 4/2016 | Wallace et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,120 B2 | 5/2017 | Lagodzki et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,918,718 B2 | 3/2018 | Lorenzo | |
| 10,149,676 B2 | 12/2018 | Mirigian et al. | |
| 10,285,710 B2 | 5/2019 | Lorenzo et al. | |
| 10,292,851 B2 | 5/2019 | Gorochow | |
| 10,420,563 B2 | 9/2019 | Hebert et al. | |
| 10,517,604 B2 | 12/2019 | Bowman et al. | |
| 10,668,258 B1 | 6/2020 | Calhoun et al. | |
| 10,806,402 B2 | 10/2020 | Cadieu et al. | |
| 10,806,461 B2 | 10/2020 | Lorenzo | |
| 2001/0049519 A1 | 12/2001 | Holman et al. | |
| 2002/0072705 A1 | 6/2002 | Vrba et al. | |
| 2002/0165569 A1 | 11/2002 | Ramzipoor et al. | |
| 2003/0009208 A1 | 1/2003 | Snyder et al. | |
| 2004/0034363 A1 | 2/2004 | Wilson et al. | |
| 2004/0059367 A1 | 3/2004 | Davis et al. | |
| 2004/0087964 A1 | 5/2004 | Diaz et al. | |
| 2006/0025801 A1 | 2/2006 | Lulo et al. | |
| 2006/0064151 A1 | 3/2006 | Guterman | |
| 2006/0100687 A1 | 5/2006 | Fahey et al. | |
| 2006/0116711 A1 | 6/2006 | Elliott et al. | |
| 2006/0116714 A1 | 6/2006 | Sepetka et al. | |
| 2006/0135986 A1 | 6/2006 | Wallace et al. | |
| 2006/0206139 A1 | 9/2006 | Tekulve | |
| 2006/0241685 A1 | 10/2006 | Wilson et al. | |
| 2006/0247677 A1 | 11/2006 | Cheng et al. | |
| 2006/0276824 A1 | 12/2006 | Mitelberg et al. | |
| 2006/0276825 A1 | 12/2006 | Mitelberg et al. | |
| 2006/0276826 A1 | 12/2006 | Mitelberg et al. | |
| 2006/0276827 A1 | 12/2006 | Mitelberg et al. | |
| 2006/0276830 A1 | 12/2006 | Balgobin et al. | |
| 2006/0276833 A1 | 12/2006 | Balgobin et al. | |
| 2007/0010850 A1 | 1/2007 | Balgobin et al. | |
| 2007/0055302 A1 | 3/2007 | Henry et al. | |
| 2007/0083132 A1 | 4/2007 | Sharrow | |
| 2007/0233168 A1 | 10/2007 | Davis et al. | |
| 2007/0270903 A1 | 11/2007 | Davis, III et al. | |
| 2008/0027561 A1 | 1/2008 | Mitelberg et al. | |
| 2008/0045997 A1 | 2/2008 | Balgobin et al. | |
| 2008/0097462 A1 | 4/2008 | Mitelberg et al. | |
| 2008/0119887 A1 | 5/2008 | Que et al. | |
| 2008/0269719 A1 | 10/2008 | Balgobin et al. | |
| 2008/0269721 A1 | 10/2008 | Balgobin et al. | |
| 2008/0281350 A1 | 11/2008 | Sepetka | |
| 2008/0300616 A1 | 12/2008 | Que et al. | |
| 2008/0306503 A1 | 12/2008 | Que et al. | |
| 2009/0062726 A1 | 3/2009 | Ford et al. | |
| 2009/0099592 A1 | 4/2009 | Buiser et al. | |
| 2009/0312748 A1 | 12/2009 | Johnson et al. | |
| 2010/0094395 A1 | 4/2010 | Kellett | |
| 2010/0114017 A1 | 5/2010 | Lenker et al. | |
| 2010/0206453 A1 * | 8/2010 | Leeflang | B29D 23/001 156/60 |
| 2010/0324649 A1 | 12/2010 | Mattsson | |
| 2011/0092997 A1 | 4/2011 | Kang | |
| 2011/0118776 A1 | 5/2011 | Chen et al. | |
| 2011/0202085 A1 | 8/2011 | Loganathan et al. | |
| 2011/0295303 A1 | 12/2011 | Freudenthal | |
| 2012/0035707 A1 | 2/2012 | Mitelberg et al. | |
| 2012/0041472 A1 | 2/2012 | Tan et al. | |
| 2012/0083868 A1 * | 4/2012 | Shrivastava | A61F 2/962 623/1.11 |
| 2012/0172913 A1 | 7/2012 | Kurrus et al. | |
| 2012/0172921 A1 | 7/2012 | Yamanaka et al. | |
| 2012/0179194 A1 | 7/2012 | Wilson et al. | |
| 2012/0283768 A1 | 11/2012 | Cox et al. | |
| 2012/0289772 A1 | 11/2012 | O'Connell et al. | |

(56) References Cited

U.S. PATENT DOCUMENTS

| | | |
|---|---|---|
| 2013/0066413 A1 | 3/2013 | Jin et al. |
| 2013/0296915 A1 | 11/2013 | Bodewadt |
| 2013/0325054 A1 | 12/2013 | Watson |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0243883 A1 | 8/2014 | Tsukashima et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalcaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |
| 2019/0192162 A1* | 6/2019 | Lorenzo ............ A61B 17/12109 |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2021/0001082 A1 | 1/2021 | Lorenzo et al. |
| 2021/0085498 A1 | 3/2021 | Nygaard et al. |
| 2021/0100555 A1 | 4/2021 | Lorenzo |
| 2021/0045759 A1 | 6/2021 | Merhi et al. |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |
| 2021/0346002 A1 | 11/2021 | Lorenzo et al. |
| 2021/0353299 A1 | 11/2021 | Hamel et al. |

FOREIGN PATENT DOCUMENTS

| | | |
|---|---|---|
| CN | 112168263 A | 1/2021 |
| EP | 1 985 244 A2 | 10/2008 |
| EP | 2498691 | 9/2012 |
| EP | 3061412 A2 | 8/2016 |
| EP | 3 092 956 A1 | 11/2016 |
| EP | 3 501 427 A1 | 6/2019 |
| EP | 3799803 A1 | 4/2021 |
| EP | 3854321 A1 | 7/2021 |
| EP | 1188414 A1 | 3/2022 |
| EP | 4119065 A1 | 1/2023 |
| JP | 2006-334408 A | 12/2006 |
| JP | 2012-523943 A | 10/2012 |

(56) References Cited

FOREIGN PATENT DOCUMENTS

| | | |
|---|---|---|
| JP | 2013-78584 A | 5/2013 |
| JP | 2014-399 A | 1/2014 |
| WO | WO 2007/070793 A2 | 6/2007 |
| WO | WO 2008/064209 A1 | 5/2008 |
| WO | WO 2009/132045 A2 | 10/2009 |
| WO | 2012/158152 A1 | 11/2012 |
| WO | WO 2016/014985 A1 | 1/2016 |
| WO | WO 2017/066386 A1 | 4/2017 |
| WO | WO 2018/022186 A1 | 2/2018 |
| WO | WO 2020/148768 A1 | 7/2020 |

* cited by examiner

IMPLANTABLE MEDICAL DEVICE DETACHMENT SYSTEM WITH FLEXIBLE BRAID SECTION

FIELD OF INVENTION

This invention generally relates to interventional medical device systems that are navigable through body vessels of a human subject. More particularly, this invention relates to detachment systems for delivering and deploying an implantable medical device to a target location of a body vessel and methods of using the same.

BACKGROUND

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, procedures using catheter deployment systems to treat an aneurysm involve inserting the distal end of a delivery catheter into the vasculature of a patient and guiding it through the vasculature to a predetermined delivery site. A vascular occlusion device, such as an embolic coil, can be attached to an implant engagement/delivery system at a distal end of a delivery member (e.g. microcatheter) which pushes the coil through the delivery catheter and out of the distal end of the delivery catheter into the delivery site. Example delivery members and engagement/delivery systems are described in U.S. Patent Publication Number 2019/0192162 A1, U.S. Patent Publication Number 2019/0328398 A1, and U.S. Patent Publication Number 2021/0001082 A1, each of which are incorporated herein by reference.

Many catheter-based implant delivery systems can include one or more inner elongated member(s) extending through the catheter that can be manipulated at the proximal end by a physician to deploy the implantable device. The inner elongated member can retain the implantable device in the catheter until the time for release of the implant. These systems can be actuated by retracting or pulling the elongated member relative to the catheter. Some of the challenges that have been associated with properly executing such aneurysm treatment procedures include ensuring the delivery member and engagement system remain in a stable position throughout a treatment. For example, in some aneurysm treatment applications, as the aneurysm becomes increasingly packed with embolic material, the delivery member can tend to shift due to increasing pushback from the embolic material being implanted. If the delivery member shifts during treatment, a physician may not be able to accurately control placement of embolic material and may choose to cease packing the aneurysm. In such an example, the aneurysm may not be sufficiently packed, which can lead to recanalization. Further, excessive movement or stretching of the delivery member and/or engagement system thereon can result in premature detachment of the embolic coil. Some examples of ways to mitigate the likelihood of premature release can result in a less flexible mechanical release system.

Additionally, catheter deployment systems can be used to treat intravascular lesions associated with intracranial atherosclerosis disease (ICAD). In some instances, an intravascular lesion may not be soft enough for a stentriever to effectively engage and remove the lesion from the blood vessel. In such case, it can be desired to deploy a stent such that the intravascular lesion can be treated by stenting. A physician may not know whether the lesion is better treated by a stent or stentriever prior to delivery of either device. Because a stentriever is retractable and a stent typically is not, in such cases, the stentriever is typically deployed in a first pass, followed by the stent (if appropriate) in a second pass. Multiple passes through vasculature can increase trauma to vasculature and increase treatment time, thereby increasing the likelihood of complications.

Thus, there is a need for systems, devices, and methods that can mitigate the likelihood of premature deployment of an intravascular treatment device while also providing a flexible mechanical release system.

SUMMARY

Generally, it is an object of the present invention to provide a detachment system for delivering an implantable medical device to a target location of a body vessel that includes a proximal delivery tube, a distal delivery tube, and a braid segment disposed between. The braid segment provides stability during the deployment of the implantable device in the aneurysm, while maximizing flexibility of the detachment system.

An example detachment system for delivering an implantable medical device to a target location of a blood vessel can include a generally hollow proximal tube, a generally hollow distal tube, a braid segment, and an engagement system. The proximal tube can include a proximal end and a distal end. The distal tube can include a proximal end, a distal end, and a compressible portion of the distal tube itself which is axially moveable from a compressed condition to an elongated condition. The braid segment can be disposed between the proximal end of the distal tube and the distal end of the proximal tube. The braid segment can be formed from a plurality of wires. The engagement system can be configured to engage and deploy the implantable medical device that is disposed at the distal end of the distal tube.

The braid segment can be concentrically disposed around a polymer liner.

A polymer sleeve can be positioned over the proximal tube, the braid segment, and at least a portion of the distal tube.

The polymer sleeve can include one or more hydrophilic coatings.

The polymer sleeve can have a wall having a thickness of between approximately 0.02 millimeters and approximately 0.08 millimeters.

The braid segment can include between approximately 8 and approximately 16 wire segments.

The braid segment can be constructed to have a pick per inch of between approximately 50 and approximately 100.

The compressible portion of the distal tube can be a spiral-cut portion of the distal tube.

The engagement system can be configured to move the compressible portion to the compressed condition when engaging the implantable medical device and deploy the implantable medical device when releasing the compressible portion to the elongated condition.

The compressible portion can be adapted to automatically move to the elongated condition when the engagement system is disengaged from the implantable medical device.

In one example, the implantable medical device can be a stentriever when engaged to the engagement system, the stentriever having a proximal end collapsed by the engagement system and a distal end collapsed by the engagement system. The implantable medical device can be a stent when disengaged from the engagement system, the stent having an open proximal end and an open distal end.

An example method of detaching an implantable medical device can include one or more of the following steps presented in no particular order. The method can further include additional steps as appreciated and understood by a person of ordinary skill in the art according to the teachings of this disclosure.

The method can include forming a compressible portion on a distal tube; forming a flexible portion on a proximal tube; attaching a braid segment to a distal end of a proximal tube and a proximal end of the distal tube; and engaging the implantable medical device with an engagement system.

The method can further include sliding a polymer sleeve over the proximal tube, the braid segment, and at least a portion of the distal tube.

The method can further include engaging the polymer sleeve to the implantable medical device.

The method can further include coating the polymer sleeve with one or more hydrophilic coatings.

The method can include wrapping the braid segment around a polymer liner prior to attaching the braid segment to the distal end of the proximal tube and the proximal end of the distal tube.

The engagement step can include using the loop wire with the locking member to engage the implantable medical device and applying force to the loop wire to move the compressible portion to the compressed condition.

The method can further include applying a force on the locking member, disengaging the implantable medical device, and allowing the compressible portion to return to the elongated condition.

The method can include deploying the implantable medical device engaged by moving the compressible portion to the elongated condition.

In one example, the implantable medical device can be a stentriever configured to expand to appose a wall of a blood vessel upon deployment.

BRIEF DESCRIPTION OF DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

A key success factor in intravascular treatment such as aneurysm treatments is for the detachment device (e.g. microcatheter) to remain stable during the deployment of an implant or other medical treatment device. During an intravascular treatment, lack of flexibility of a distal portion of a detachment device can cause the detachment device to pull back from the treatment site or otherwise move out of position while the implant is being placed in an aneurysm or other treatment site. A detachment device having a more flexible distal portion can therefore provide a stable system for delivering medical devices in neurovascular anatomy in addition to other applications facing a similar challenge. Flexible structures, however can tend deform, extend, or expand when navigating tortuous anatomy. Deformation of the detachment system can inhibit the detachment system's ability to navigate to a treatment site and/or effectively deploy the medical device. Elongation of the detachment system can result in premature deployment of the medical device. An object of the present invention is to provide a detachment system having a highly flexible braided segment that is stretch resistant and structurally stable throughout delivery and deployment of a medical treatment device.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature can be that of any "subject" or "patient" including of any human or animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The figures illustrate a generally hollow or tubular structure according to the present invention. When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

FIGS. 1A-3B illustrate examples of detachment system 10 wherein is disclosed herein and addresses these and other drawbacks of previous approaches. The detachment system 10 can include a proximal delivery tube 100 and a distal delivery tube 300. A braid segment 200a, 200b, 200c can be disposed between the proximal delivery tube 100 and the distal delivery tube 300. The braid segment 200a, 200b, 200c can be formed from a plurality of wires 202. The braid segment 200b can be wrapped around a polymer liner 204 to minimize friction when delivering the detachment 10 and to protect the braid segment 200b. A polymer sleeve 206 can be disposed over the braid segment 200c to further minimize friction and protect the braid segment 200c. The braid segment 200a, 200b, 200c allows the detachment system 10 to remain stable during deployment of the implantable medical device 12 while also providing sufficient flexibility that minimizes the potential of the detachment system 10 to move or pull back out of position while the implantable medical device is being positioned in an aneurysm.

Examples of detachment systems 10 of the present invention, as illustrated in FIGS. 1A through 3B can have a proximal elongated delivery tube 100, a braid segment 200a, 200b, 200c, and a distal delivery tube 300. An implantable medical device 12 can be engaged at the distal end 304 of the distal delivery tube 300. The implantable medical device 12 can be an embolic coil. The implantable medical device 12 can be a stent retriever 612 as illustrated in FIGS. 6A, 6B, 7A, 7B, 8A through 8C, alternative thereto, or variation thereof. Although the implantable medical device 12 is illustrated as an embolic coil or a stent retriever 612 herein, it will be appreciated that virtually any implantable medical device 12 may be delivered and deployed by the detachment system 10 according to the present invention. The implantable medical device 12 can be engaged to the detachment system 10 using a locking member 140 and a loop wire 400. The implantable medical device 12 can have a locking portion 18 to interface with an engagement system 140, 400.

The proximal delivery tube 100 can have a proximal end portion 102, a distal end portion 104, and a flexible portion 106. The flexible portion 106 can be disposed between the proximal end portion 102 and the distal end portion 104. The proximal delivery tube 100 can have an axial lumen therein. The distal delivery tube 300 can have a proximal end portion 302, a distal end portion 304, and a compressible portion 306. The compressible portion 306 can be disposed between the proximal end portion 302 and the distal end portion 304. The compressible portion 306 can be closer to the distal end portion 304. The distal delivery tube 300 can form an axial lumen therein.

The delivery tubes 100, 300 can be made of a biocompatible material, such as stainless steel. The tubes 100, 300 can have a diameter of between about 0.25 millimeters (0.010 inch) and about 0.46 millimeters (0.018 inch). In one example, the delivery tubes can have a diameter of approximately 0.37 millimeters (0.0145 inch). These examples of tube size are suitable for delivering and deploying embolic coils to target locations, typically aneurysms, within the neurovasculature. It is contemplated that differently sized tubes 100, 300 comprised of other materials can be useful for different applications and are within the scope of the present invention.

The flexible portion 106 of the proximal delivery tube 100 can allow the proximal delivery tube 100 to bend and flex. This ability can assist tracking the detachment system 10 through the catheter and the tortuous path through the human vasculature. The flexible portion 106 can be formed with interference spiral cuts. These cuts can allow for gaps to permit bending but in one example, do not act as a spiral-cut spring. In this configuration, the interference spiral cuts can bend and flex but do not compress.

The compressible portion 306 is axially adjustable between an elongated condition and a compressed condition. The compressible portion 306 can be formed from a spiral-cut portion of the distal tube 300 by a laser-cutting operation. However, it is contemplated that any other arrangement allowing axial adjustment (e.g., a wound wire or spiral ribbon) is also suitable for use with detachment systems according to the present invention. The compressible portion 306 can be in the elongated condition at rest and automatically or resiliently return to the elongated condition from a compressed condition, unless otherwise constrained. The detachment device 10 can include a loop wire 400 that together with the locking member 140 are configured to secure the implant 12 to the detachment device 10. The compressible portion 306 can be maintained in a compressed condition via tension in the loop wire 400 when the loop wire 400 and locking member 140 are engaged to the implant 12. The loop wire 400 can be affixed to the distal tube 300 near the proximal end 302 of the distal tube 300.

The braid segment 200a, 200b, 200c can be disposed between the proximal end 302 of the distal tube 300 and the distal end 104 of the proximal tube 100. The braid segment 200a, 200b, 200c can be affixed to the proximal end 302 of the distal tube 300 and the distal end 104 of the proximal tube 100. The braid segment 200a, 200b, 200c can be affixed to the proximal end 302 of the distal tube 300 and the distal end 104 of the proximal tube 100 using any attachment mechanism including but not limited to, adhesives, welding, or the like. The proximal tube 100 can extend a majority of the length of the detachment system 10, while the braid segment 200a, 200b, 200c and the distal tube 300 can extend over the most distal portion of the detachment system. In one example, the braid segment 200a, 200b, 200c and the distal tube 300 can extend over the most distal 500 millimeters of the detachment system 10.

The braid segment 200a, 200b, 200c can be formed from a plurality of wires 202. The plurality of wires 202 can be made of a biocompatible material, such as stainless steel or nitinol. The plurality of wires 202 can include round wires. Alternatively or in addition to, the plurality of wires 202 can include flat wires. The plurality of wires 202 can include between approximately 6 wires to approximately 20 wires. The braid segment 200a, 200b, 200c can be constructed with various picks per inch. In one example, the braid segment 200a, 200b, 200c can be constructed with between approximately 50 picks per inch to approximately 100 picks per inch. The number of wires in the plurality of wires 202 and the picks per inch can result in the braid segment 200a, 200b, 200c having a reduced cross-section dimension prior to kinking when a hollow member is bent. By reducing a cross-section dimension, the braid segment 200a, 200b, 200c can be substantially oval shaped. The number of wires in the plurality of wires 202 and the picks per inch can facilitate elongation of the braid segment 200a, 200b, 200c such that the braid segment 200a, 200b, 200c can resist stretching when the detachment system 10 is withdrawn in a blood vessel BV while the implant 12 is held in the aneurysm by friction. Additionally, elongation of the braid segment 200a, 200b, 200c can inhibit the braid segment 200a, 200b, 200c from compressing axially or radially collapsing when the compressible portion 106, 206, 306 is in a compressed configuration prior to deployment.

When the detachment device 10 is assembled, the braid segment 200a, 200b, 200c can be more flexible than the proximal tube 100 and the distal tube 300. One way to measure flexibility is to perform a three-point bend test wherein a portion of a detachment system 10 is held fixed at two end points, a force is applied perpendicularly to the detachment system 10 centrally between the points, and flexibility is quantified by the length of deflection of the detachment system 10 caused by the force. When measured this way, in some examples, the braid section 200a, 200b, 200c can be more flexible than the distal tube 300 and more flexible than the proximal tube 100. In other words, when the three-point test is performed identically on the three sections 100, 200a, 200a, 200c, 300, the braid segment 200a, 200b, 200c can deflect over a length that is greater than the deflection length of the distal tube 300 and greater than the length of deflection of the proximal tube 100. Flexibility can be measured in other ways as would be appreciated and understood by a person of ordinary skill in the art.

The flexible braid segment 200a, 200b, 200c can be more flexible than the relatively stiff proximal tube 100 and the relatively flexible distal tube 300. The relatively stiff proximal tube 100 extending a majority of the length of the detachment system 10 can resist kinking while being pushed through a microcatheter. The flexible braid 200a, 200b, 200c and the distal tube 300 can each be sufficiently flexible to reduce the effects of push-back when the implantable medical device 12 is being placed in an aneurysm. Because the flexible braid segment 200a, 200b, 200c does not have to be compressible resilient like the distal tube, the flexible braid segment 200a, 200b, 200c can have greater flexibility than the distal tube 300. By varying the pick per inch, the number of wire segments, and/or the size of each of the wire segments in the plurality of wires 202, compressibility and elongation of the detachment system 10, including the flexible braid segment 200a, 200b, 200c can be precisely manipulated and/or controlled.

Figure 1A:
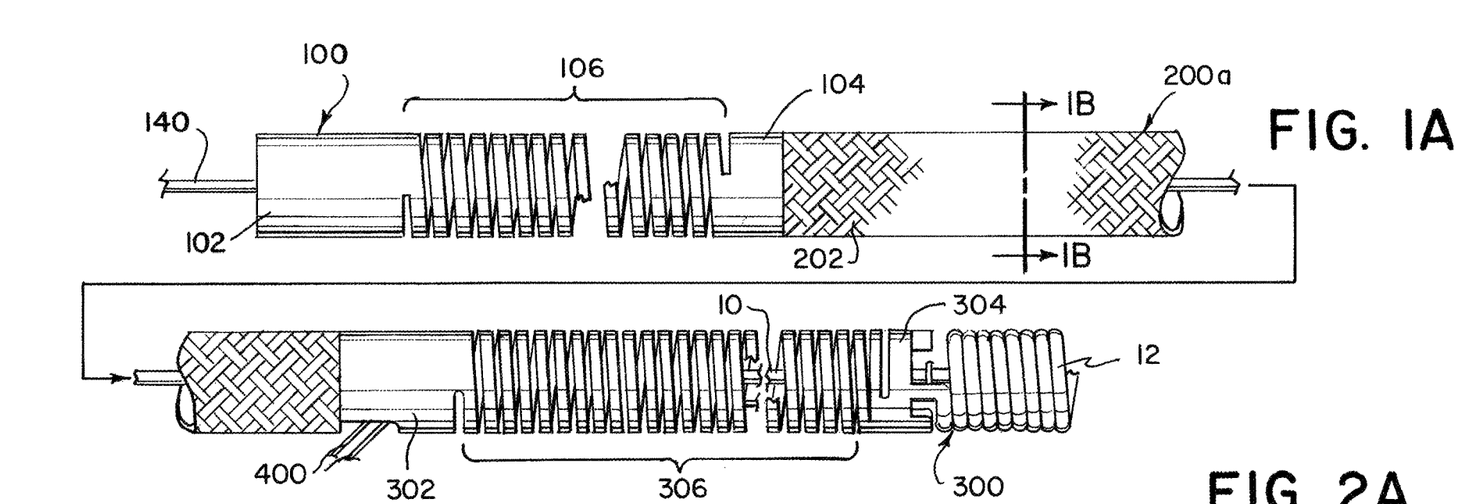
FIG. 1A is an illustration of an example detachment system having a braid segment and FIG. 1B is a cross-sectional view of the example detachment system of FIG. 1A, according to aspects of the present invention.
Figure 1B:
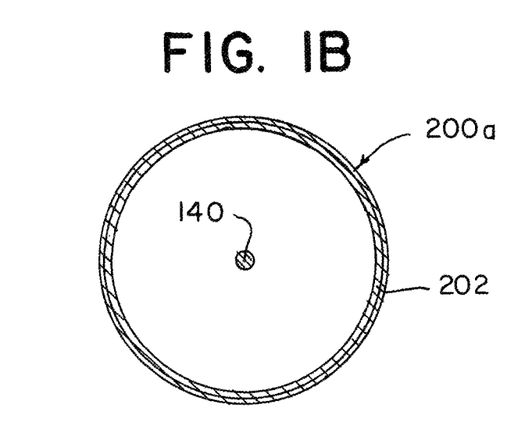

As illustrated in FIGS. 1A and 1B, the braid segment 200a can disposed between the proximal tube 100 and the distal tube 300. The locking member 140 can be disposed within a lumen of the braid segment 200a. The locking member 140 can be translatable at least in the proximal direction in relation to the distal end 304 of the distal tube 300. The plurality of wires 202 of the braid segment 200a can be exposed. In this configuration, the braid segment 200a is not covered by a polymer sleeve 206 or any other protective covering. In this configuration, the plurality of wires 202 can be exposed to the interior walls of blood vessels during delivery of the detachment system 10 to the desired location in the patient.

Figure 2A:
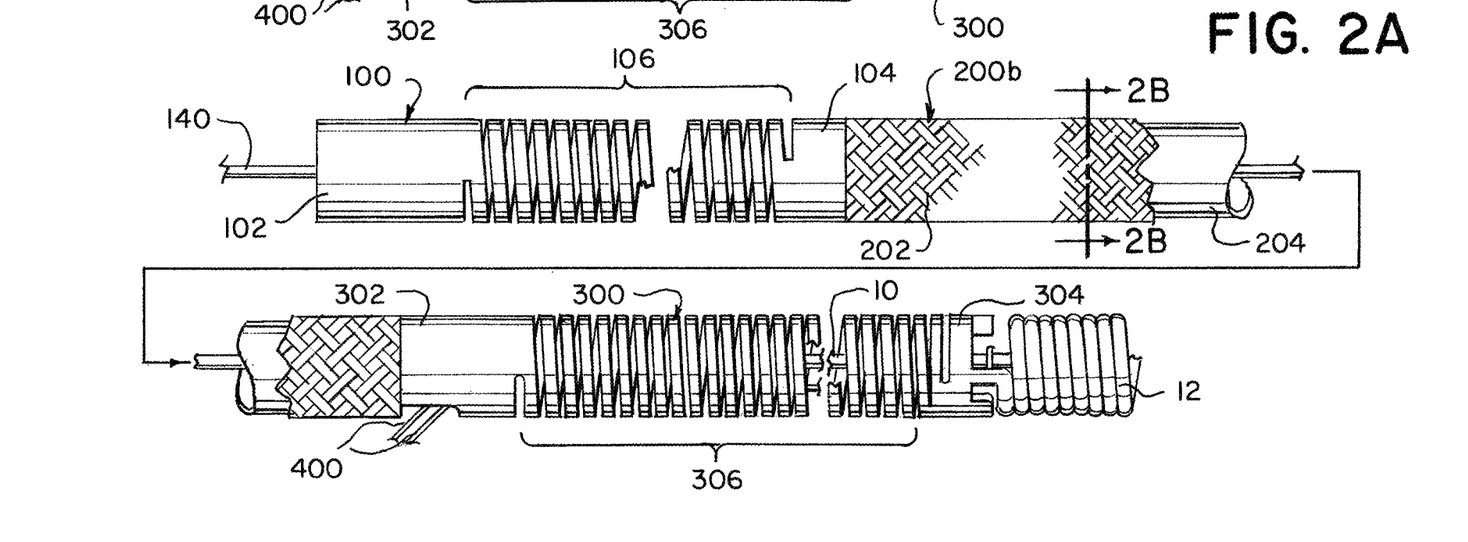
FIG. 2A is an illustration of an additional example detachment system having a braid segment, according to aspects of the present invention.

FIG. 2A illustrates the detachment system 10 having a braid segment 200b concentrically disposed around a polymer liner 204. The polymer liner 204 can be a polytetrafluoroethylene (PTFE) liner. The polymer liner 204 can provide stability to the braid segment 200b and reduce friction between the braid segment 200b and the locking member 140 disposed within the lumen of the braid segment 200b. The braid segment 200b can be wrapped around the polymer liner 204 prior to the braid segment 200b and polymer liner 204 being attached to the proximal tube 100 and the distal tube 300 or the polymer liner 204 can be a separate entity placed inside the entire length of the device including the at least a portion proximal tube 100, at least a portion of the distal tube 300 and at least a portion of the braid segment 200b.

Figure 2B:
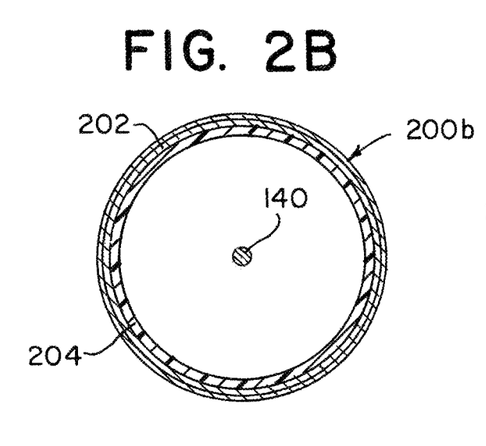
FIG. 2B is a cross-sectional view of the example detachment system of FIG. 2A, according to aspects of the present invention.

FIG. 2B illustrates a cross-sectional view of the braid segment 200b wrapped around the polymer liner 204. The polymer liner 204 can have substantially the same shape as the proximal tube 100 and the distal tube 300. The polymer liner 204 can be substantially tubular and can have a lumen disposed therethrough. The locking member 140 can be slidably disposed within the lumen of the polymer liner 204.

Figure 3A:
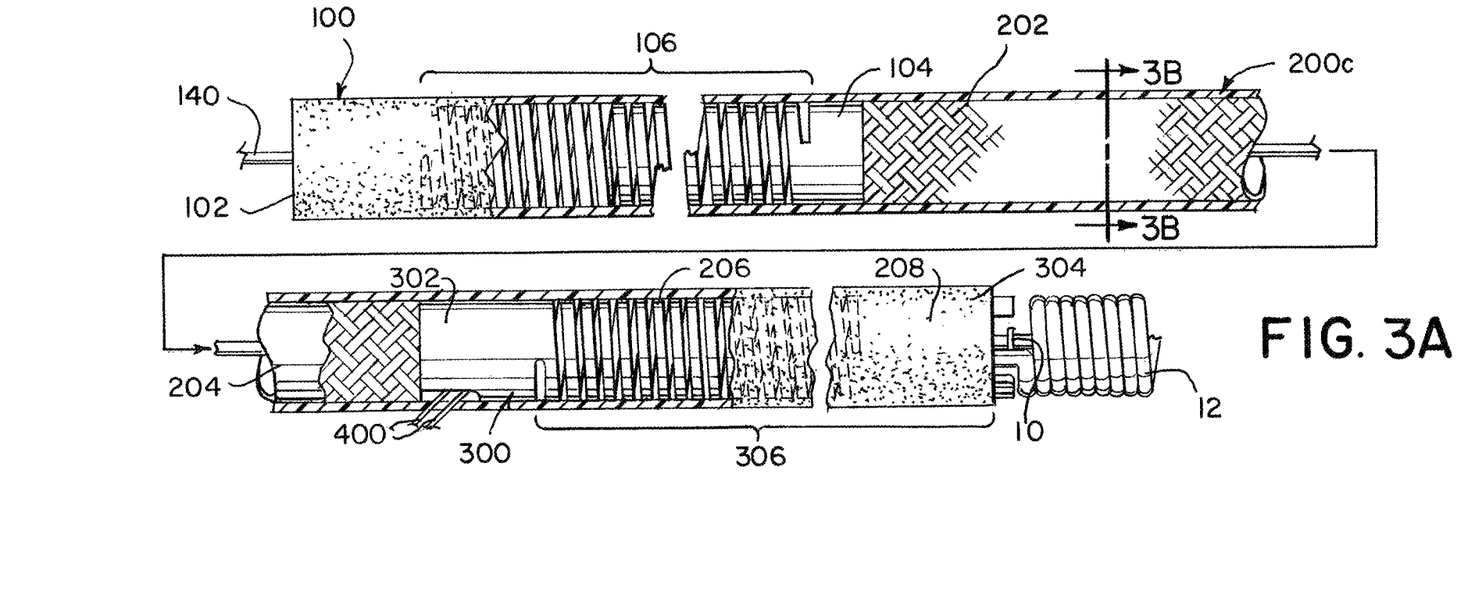
FIG. 3A is an illustration of an additional example detachment system, according to aspects of the present invention.

FIG. 3A illustrates the detachment system 10 having a braid segment 200c surrounded by a polymer liner 204 and a polymer sleeve 206 positioned over at least a portion of the proximal tube 100, the braid segment 200c, and at least a portion of the distal tube 300. The polymer sleeve 206 can be slidably disposed over the at least a portion of the proximal tube 100, the braid segment 200c, and at least a portion of the distal tube after assembly of the detachment system 10. In one example, the polymer sleeve 206 can be positioned over at least a portion of the flexible section 106 of the proximal tube 100 to inhibit deformation of the flexible section and/or reduce friction with vasculature and the flexible section 106 during intravascular navigation. In one example, the polymer sleeve 206 can be positioned over the entire distal tube 300 such that the polymer sleeve 206 can be affixed proximate to the implantable medical device 12. In one example, the polymer sleeve 206 can be glued to the distal tube 300 and/or proximal tube 100. Alternatively or in addition to, the polymer sleeve 206 can be fused over the braid segment 200c such that the polymer sleeve 206 can be incorporated into the braid segment 200c. The polymer sleeve 206 can be affixed to the implantable medical device 12 using an attachment mechanism including adhesives, fusion, welding, or the like. The polymer sleeve 206 can be a thermoplastic elastomer sleeve. The polymer sleeve 206 can include one or more additives to increase lubricity so that the sleeve can easily slide through a body vessel.

The polymer sleeve 206 can provide stability to the braid segment 200c and reduce friction while delivering the detachment system 10 to the desired location in a patient. The polymer sleeve 206 can protect the braid segment 200c as the detachment system 10 is transported through the vasculature and to the desired location in a patient.

Figure 3B:
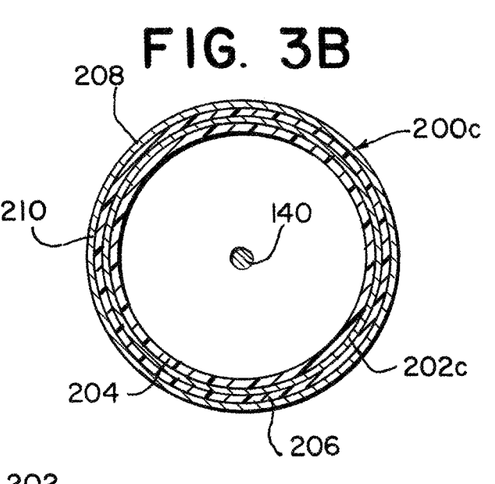
FIG. 3B is a cross sectional view of the example detachment system of FIG. 3A, according to aspects of the present invention.

FIG. 3B illustrates a cross-sectional view of the detachment system 10 illustrated in FIG. 3A. The polymer sleeve 206 can have a wall 210 with a thickness between approximately 0.02 millimeters to approximately 0.08 millimeters. In one example, one or more hydrophilic coatings 208 can be applied to the polymer sleeve 206. The one or more hydrophilic coating 208 can include hyaluronic acid, polyalkylene glycols, alkoxy polyalkylene glycols, poly(saccharide), poly(vinylpyrrolidone), poly(vinyl alcohol), poly(acrylic acid), poly(acrylamide), poly(maleicanhydride), copolymers thereof and mixtures thereof. The one or more hydrophilic coating 208 can further minimize friction that can occur when delivering the detachment system 10 through the vasculature and to the desired location in a patient.

As illustrated in FIGS. 2A and 2B, the braid segment 200c can include a polymer liner 204. The braid segment 200c can be concentrically disposed around the polymer liner 204. The polymer liner 204 can provide stability to the braid segment 200c and reduce friction between the braid segment 200c and the locking member 140.

As illustrated in FIG. 3B, the locking member 140 can be translatable through the lumens of the proximal delivery tube 100 and the braid segment 200c. The locking member 140 can further be translatable through the lumen of the distal delivery tube 300, as illustrated in FIG. 3A.

Although FIGS. 3A and 3B illustrate the detachment system 10 having a braid segment 200c concentrically disposed around a polymer liner 204 and a polymer sleeve 206 disposed over the at least a portion of the proximal tube 100, the braid segment 200c, and at least a portion of the distal tube after assembly of the detachment system 10, it is contemplated that in some instances the braid segment 200c is not disposed around the polymer liner 204.

Figure 4A:
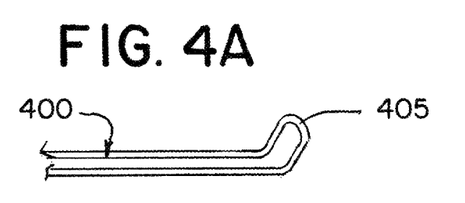
FIG. 4A is a side perspective view of an example of a loop wire, according to aspects of the present invention.
Figure 4B:
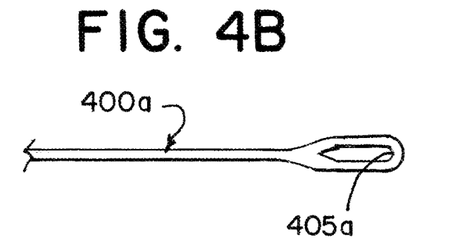
FIG. 4B is a plane view of an example of a loop wire according to aspects of the present invention.
Figure 4C:
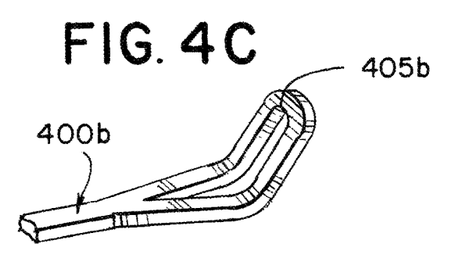
FIG. 4C is rear perspective detail view of an opening of the loop wire in an up-turned condition, according to aspects of the present invention.

FIGS. 4A through 4C illustrate examples of the loop wire 400. The loop wire 400 can be relatively small, having the thickness of a hair in some examples. Because of the small size of the loop wire 400, the loop wire 400 can be entirely shielded by the distal end 304 of the distal delivery tube 300 to prevent damage from accidental contact. The loop wire 400 can be an elongated wire that is looped, as illustrated in FIG. 4A. The loop wire 400a can also be a single elongated wire with an opening 405, as illustrated in FIG. 4B. The opening 405 can be formed by loosely bending the loop wire 400a in half. In an alternative example, the loop wire 400b can include a flat ribbon defining an opening 405b at a distal portion and the opening 405b can be in an up-turned condition suitable for engaging an end of the implantable medical device 12. An example of the loop wire 400, 400a, 400b can be elastically deformable to the up-turned condition such that it will return to the substantially flat condition when not otherwise constrained. The loop wire 400, 400a, 400b can be formed from of any of a number of materials, including nitinol and stainless steel.

To load the detachment system 10, the locking member 140 can be inserted axially within the lumens of the proximal tube 100, the braid segment 200a, 200b, 200c, and the distal tube 300. A distal end 404 of the loop wire 400 can be inserted into the distal delivery tube 300 through an anchor portion located proximate the proximal end 302 of the distal tube 300. The loop wire 400 can be passed through the lumen of the distal tube 300 to the distal end 304. The distal end 404 of the loop wire 400 can then be looped to form the opening 405. The opening 405 can be passed through the locking portion 18. The locking member 140 can be passed through the opening 405 to engage the medical device 12.

Figures 5A, 5B:
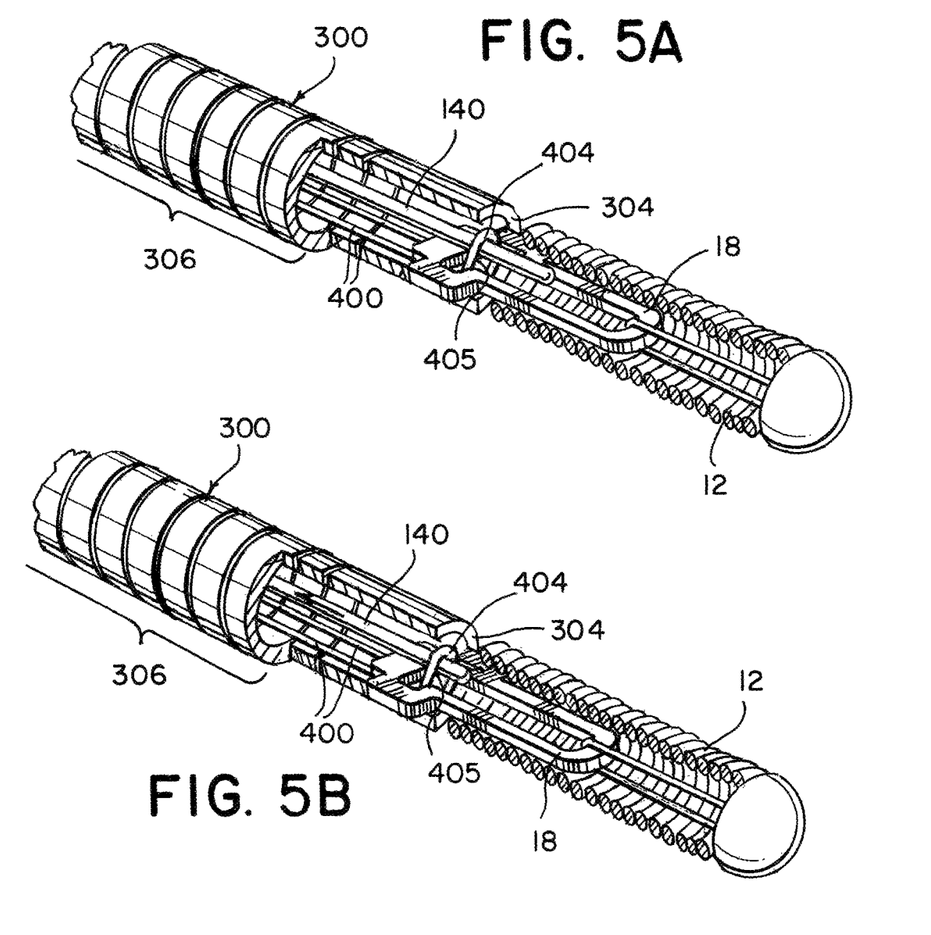
FIGS. 5A-5D are a series of illustrations of an example implantable medical device being detached, according to aspects of the present invention.

FIGS. 5A through 5D, illustrate the detachment of the implantable medical device 12 where the implantable medical device 12 is an embolic coil. FIG. 5A illustrates the detachment system 10 with the implantable medical device 12 engaged and the compressible portion 306 of the distal tube 300 in the compressed state. To reach the compressed state, the loop wire 400 can be pulled taught at a proximal end of the loop wire 400 and continued force can compress the compressible portion 306. The amount of compression can be controlled by the amount of force applied to the proximal end of the loop wire 400 after the medical device 12 is mounted to the distal end 304 of the distal tube 300. Once the distal tube 300 is compressed the appropriate amount, the loop wire 400 can be anchor welded at a wire weld point proximate the proximal end 302 of the distal tube 300 or proximate to the anchor portion of the distal tube 300.

In FIG. 5A, the engagement system, including the locking member 140 and the loop wire 400, is locked into the locking portion 18 of the medical device 12. The opening 405 of the loop wire 400 can be inserted through the locking portion 18. When the locking member 140 is inserted through the opening 405 the implantable medical device 12 can be securely in the desired position.

FIG. 5B illustrates the locking member 140 being drawn proximally to begin the release sequence for the implantable medical device 12, as indicating by the arrow.

Figures 5C, 5D:
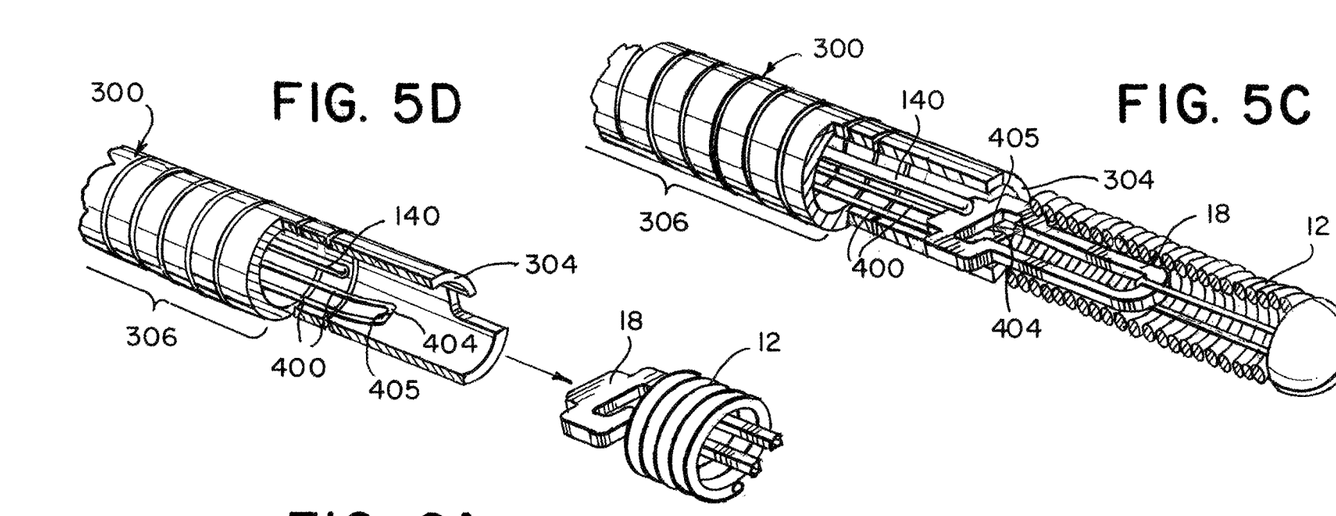

FIG. 5C illustrates the instant the locking member 140 exits the opening 405 and is pulled free of the loop wire 400. At this instant, the distal end 404 of the loop wire 400 can return to its original, preformed shape and can exit the locking portion 18. Once, the loop wire exits the locking portion 18, no component is holding the implantable medical device 12 to the detachment system 10.

FIG. 5D illustrates the end of the release sequence. The compressible portion 306 can expand and return to its original, elongated condition. When the compressible portion 306 returns to its original, elongated condition, the compressible portion 306 can "spring" forward. An elastic force E can be imparted by the distal end 304 of the distal tube 300 to the implantable medical device 12 to "push" it away to ensure a clean separation and delivery of the medical device 12 to the desired location.

Figure 6A:
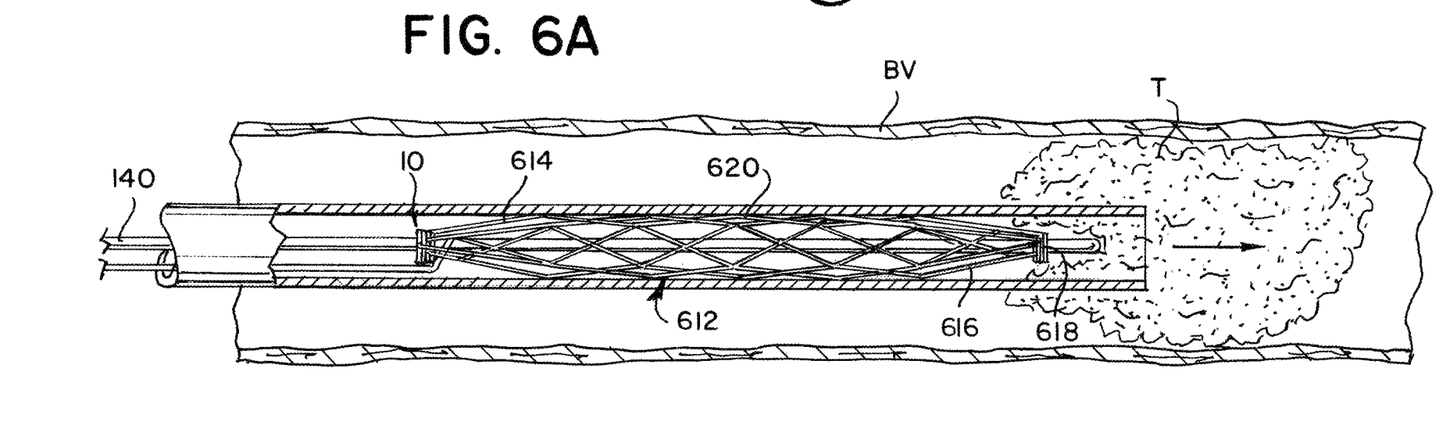
FIGS. 6A-6C are a series of illustrations of deployment an example stentriever as the implantable medical device, according to aspects of the present invention.
Figure 6B:
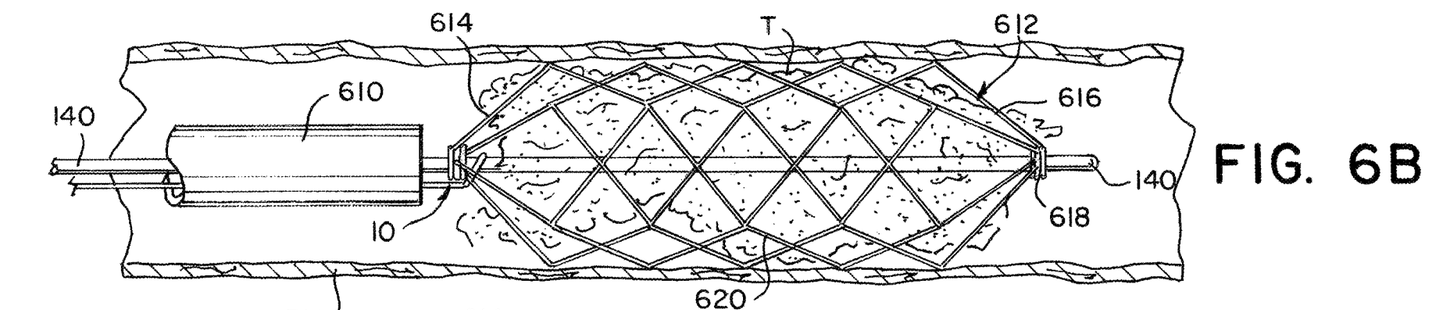
Figure 6C:
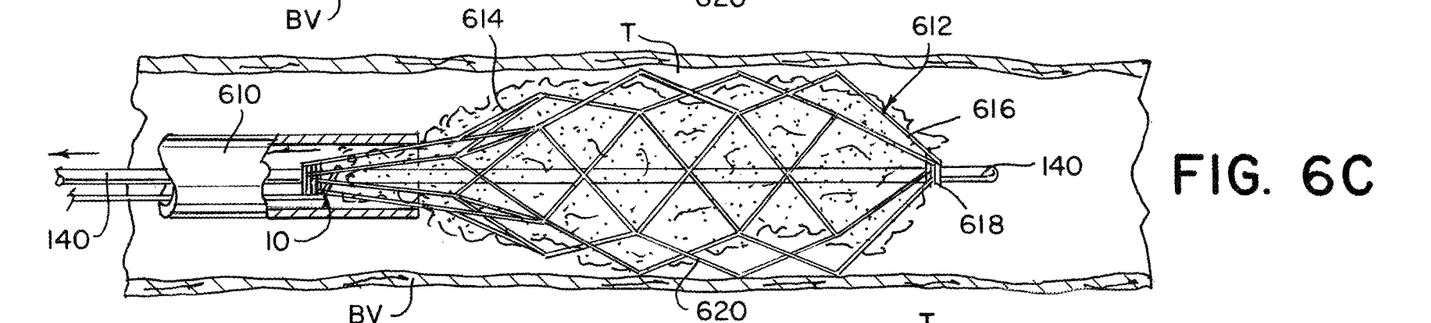

FIGS. 6A through 6C illustrate an example treatment method of a thrombus T or lesion within a blood vessel BV using the same detachment device 10 as illustrated in FIGS. 1A through 3B and a stentriever 612 as the medical implant 12. The stentriever 612 can have a proximal end 614 and a distal end 616. The proximal end 614 of the stentriever 612 can be affixed to the detachment device 10. The locking member 140 can extend through the distal end 616 of the stentriever 612, as illustrated in FIG. 6A. The detachment device 10 and the stentriever 612 can be disposed within a microcatheter 610 during delivery through the vasculature. The microcatheter 610 can prevent the strut framework 620 of the stentriever 612 from self-expanding. In some instances, the microcatheter 610 can cross a thrombus T or lesion within a blood vessel BV. The microcatheter 610 can be sized to maintain the stentriever 612 collapsed thereon as the microcatheter 610 and stentriever 612 are positioned across the thrombus T. The stentriever can be maintained in position as the microcatheter 610 is retracted proximally to allow the stentriever 612 to expand to appose the walls of the blood vessel BV.

FIGS. 6B and 6C illustrate the microcatheter 610 can be drawn proximally to allow the strut framework 620 of the stentriever 612 to begin to expand. The strut framework 620 can self-expand to appose the walls of the blood vessel BV. The stentriever 612 can include loops 618 disposed at the distal end 616 and the proximal end 614. The locking member 140 extending through the distal end 616 of the stentriever 612 can engage with the loops 618, such that the distal end 616 and the proximal end 614 of the stentriever 612 remain closed. By maintaining the distal end 616 and the proximal end 614 in a closed configuration via the loops 618 engaging with the locking member 140, when the stentriever 612 expands, it can form a substantially conical or tubular shape. Upon expanding, the strut framework 620 can engage and expand through soft material of the thrombus T. The detachment device 10 affixed to the proximal end 614 of the stentriever 612 can then be used to facilitate removal of the stentriever 612 including the captured thrombus T from the blood vessel BV. The detachment device 10 and the stentriever 612 with the captured thrombus T can be retracted proximally, such that the thrombus T can be effectively removed from the blood vessel BV.

Upon crossing the affected area including the thrombus T and/or lesion, in some treatments, the thrombus material may be sufficiently soft to pass through the strut framework 620 of the stentriever as illustrated in FIGS. 6B and 6C. In such cases, the stentriever 612 can remain attached to the detachment device 10 as the captured thrombus T, stentriever 612, and detachment device 10 are pulled proximally from patient. The removal of the stentriever 612 and thrombus T from the patient can be performed with adjunctive aspiration through a larger diameter intermediate catheter positioned over the microcatheter with its tip in close proximity to the proximal end 614 of the stentriever 612. Alternatively, the thrombus material may not be sufficiently soft to pass through the strut framework 620, or there may be an underlying narrowing (stenosis) of the blood vessel BV after removal of the thrombus T that continues to restrict flow beyond the lesion, in which case the affected area may be better treated by stenting.

Figure 7A:
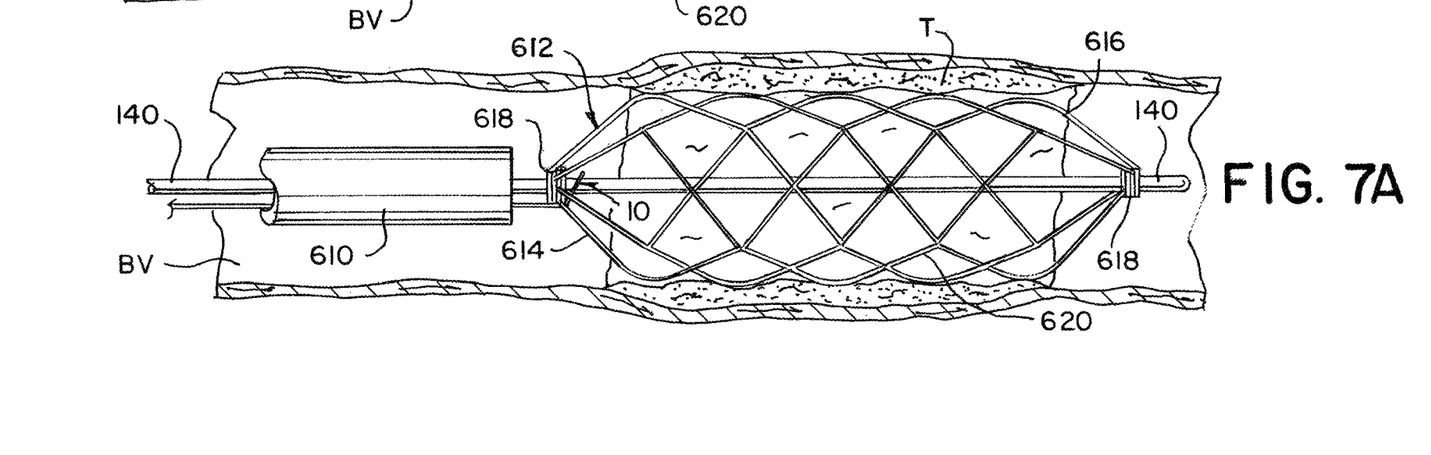
FIGS. 7A-7B are a series of illustrations of an example stentriever being detached, according to aspects of the present invention.
Figure 7B:
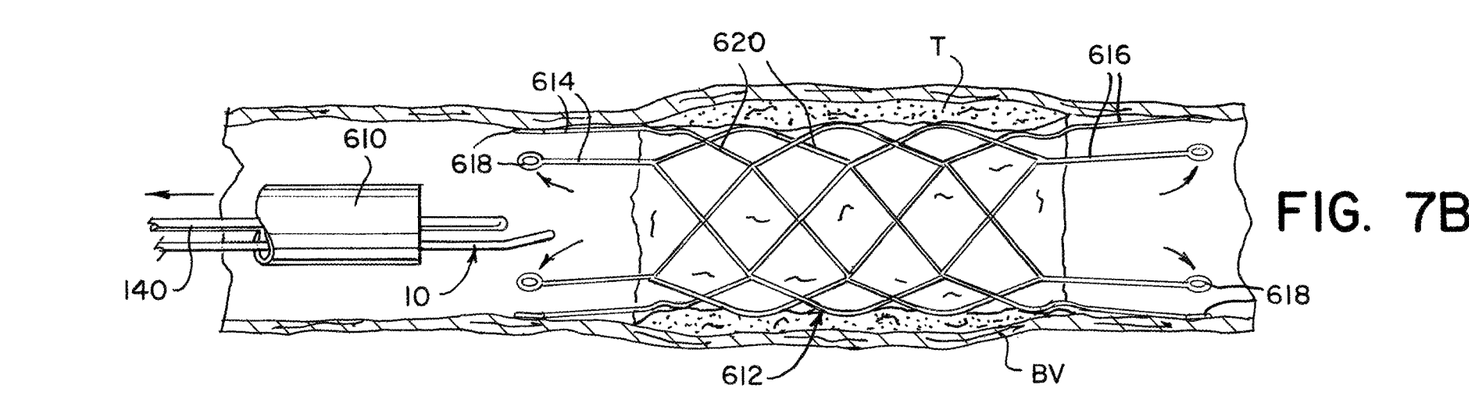

FIGS. 7A and 7B illustrate an additional treatment method using the detachment device 10 and the stentriever 612 that can be applied when stenting is appropriate. As illustrated in FIG. 7A, when the microcatheter 610 is drawn proximally, the stentriever 612 can begin to expand. As the stentriever 612 expands, the stentriever 612 can press against the thrombus T, causing the thrombus T to press against the walls of the blood vessel BV. The distal end 616 and/or the proximal end 614 of the stentriever can include loops 618 sized to allow the locking member 140 to pass through. The loops 618 can be placed at intervals circumferentially around the stentriever 612 so that when the locking member 140 is extended through the loops, the distal end 616 and/or the proximal end 614 has a conical shape, extending inward toward the locking member 140 as illustrated. As the locking member 140 is drawn proximally, the closed distal end 616 of the stentriever 612 can be released, as the loops 618 disengaged with the locking member 140. Once released, the distal end 616 can open such that the distal end 616 can appose the walls of the blood vessel BV. As the locking member 140 is further drawn proximally, the closed proximal end 614 of the stentriever 612 can also be released. The proximal end 614 can then open such that the proximal end 614 can appose the walls of the blood vessel BV. In this configuration, the stentriever 612 is converted into a permanently implantable stent which can continue to press the thrombus T against the blood vessel BV, as well as apply a chronic force against the wall of the blood vessel BV to open any underlying stenosis with or without the aid of a subsequently applied angioplasty balloon dilation.

As illustrated in FIG. 7B, the stentriever 612 can be detached from the detachment device 10. Once detached, the "stentriever" 612 is no longer retrievable from the body and thereby is, effectively, a stent. The method of detachment of the stentriever 612 can be the same detachment method as illustrated in FIGS. 5A through 5D. Once deployed, the stentriever (stent) 612 can remain across the blood vessel BV.

Figure 8A:
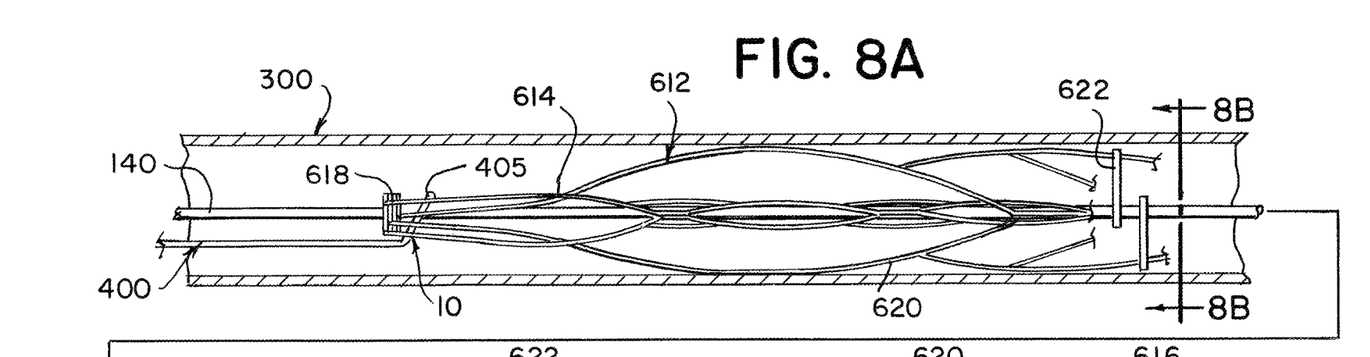
FIGS. 8A-8C are illustrations of an additional example stentriever attached to a deployment system (FIG. 8A), in cross-section (FIG. 8B), and being detached from the deployment system (FIG. 8C), according to aspects of the present invention.
Figure 8B:
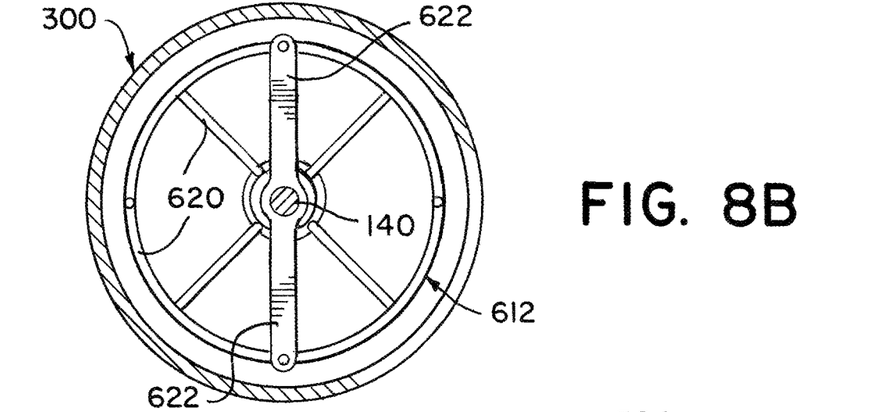
Figure 8C:
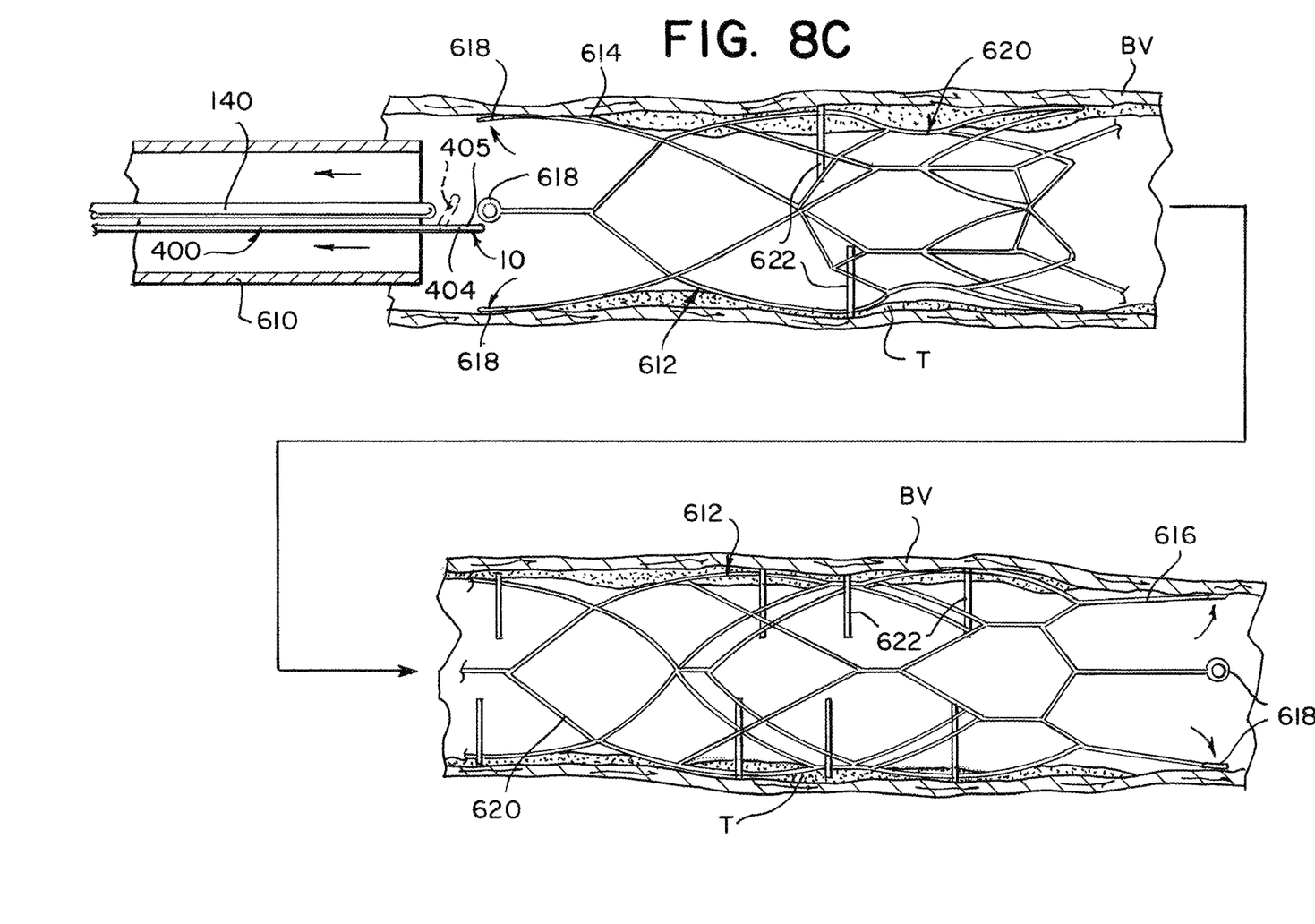

FIGS. 8A through 8C illustrate deployment and optional detachment of an additional example stentriever 612 using a similar detachment method and detachment device 10 as illustrated in FIGS. 5A through 5D. The stentriever 612 can have a proximal end 614 and a distal end 616. The proximal end 614 can be affixed to the detachment device 10, and more particularly to the distal end 304 of the distal tube 300. When the stentriever 612 is affixed to the detachment device 10 prior to deployment, the compressible portion 306 of the distal tube 300 can be in the compressed state.

As illustrated in FIG. 8A, the engagement system 140, 400 can be engaged with the stentriever 612. The locking member 140 can extend to a distal end 616 of the stentriever 612 such that the locking member 140 extends through the opening 405 of the loop wire 400. The stentriever 612 can include loops 618 similar to as illustrated and described in FIGS. 7A and 7B. The stentriever 612 can, but need not, include a locking portion 18 having a geometry as illustrated in FIGS. 5A and 5B. As illustrated in FIG. 8A, the loop wire 400 can be fed through the stentriever 612 near the proximal end of the stentriever 612 so that the engagement between the loop wire 400, locking member 140, distal tube 300, and stentriever 612 are configured to secure the stentriever to the detachment device 10. The stentriever 612 can further include eyelets 622 configured to maintain compression of the body of the stentriever 612 during delivery. The eyelets 622 can be shaped similar to the loops 618. The eyelets 622 and loops 618 can include openings sized to allow the locking member 140 to pass therethrough. The one or more eyelets 622 can be affixed to the expandable framework 620 and positioned at least partially around the locking member 140 such that the expandable framework 620 is prevented from pre-maturely deploying and the stentriever 612 is securely engaged with the engagement system 140, 400. In this configuration, the expandable framework 620 can be prevented from expanding even without the use of a catheter. In one example, the one or more eyelets 622 can be disposed along the entire stentriever 612. Alternatively, the one or more eyelets can be disposed along a portion of the stentriever 612. By way of example, the one or more eyelets 622 can be disposed along a distal portion of the stentriever 612. FIG. 8B illustrates a cross-sectional view of the example stentriever 612 as illustrated in FIG. 8A. The stentriever 612 can be affixed to the distal tube 300, such that the stentriever 612 is engaged with the detachment system 10. The locking member 140 can be translatable through the distal tube 300 and can extend through the stentriever 612. The expandable framework 620 of the stentriever 612 can include one or more eyelets 622. As illustrated in FIG. 8B, the eyelets 622 can be affixed at least partially around the locking member 140 and to the expandable framework 620 such that the stentriever 612 is prevented from expanding pre-maturely.

FIG. 8C illustrates the locking member 140 can be drawn proximally to begin the release sequence for the stentriever 612, as indicating by the arrow. When the locking member 140 is proximally drawn, the loops 618 at the distal end 616 are released, then the eyelets 622 are released. As the loops 618 and eyelets 622 are released, the expandable framework 620 of the stentriever 612 can begin to expand. By way of example, as the locking member 140 is proximally drawn, the eyelets 622 disposed proximate the open distal end 616 of the stentriever 612 can be first released, such that the open distal end 616 stentriever 612 can begin to expand. As the locking member 140 is further proximally drawn, the eyelets 622 disposed proximate the proximal end 614 of the stentriever 612 can be released, such that the open proximal end 614 of the stentriever 612 can expand.

At the instant the locking member 140 exits the opening 405 and is pulled free of the loop wire, the distal end 404 of the loop wire 400 can return to its original, preformed shape. At this point in the release sequence, no component is holding the stentriever 612 to the detachment system 10, as all the eyelets 622 affixed to the expandable framework 620 are released.

After release of the stentriever 612, the compressible portion 306 can expand and return to its original, elongated condition. When the compressible portion 306 returns to its original, elongated condition, the compressible portion 306 can "spring" forward. An elastic force can be imparted by the distal end 304 of the distal tube 300 to the stentriever 612 to "push" it away to ensure a clean separation and delivery of the stentriever 612 to the desired location. Upon detachment, the stentriever 612 can fully expand such that the stentriever 612 can appose the walls of the blood vessel.

Figure 9:
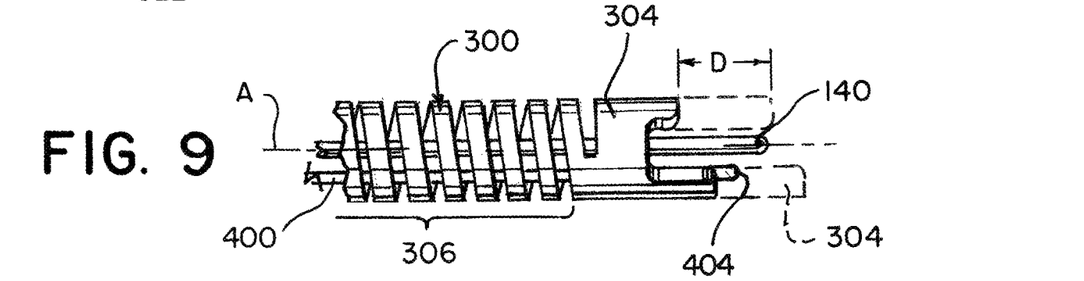
FIG. 9 is a side view of an example of the distal tube in the compressed and expanded state, according to aspects of the present invention.

FIG. 9 illustrates the distal tube 300 without the implantable medical device 12 in a compressible condition and an elongated condition. The compressible portion 306 can be shortened in axial length to the compressed condition. The compressible portion 306 can be shorted in axial length a distance D when moving from the elongated condition to the compressed condition. This compression can occur along the axis A.

Figure 10:
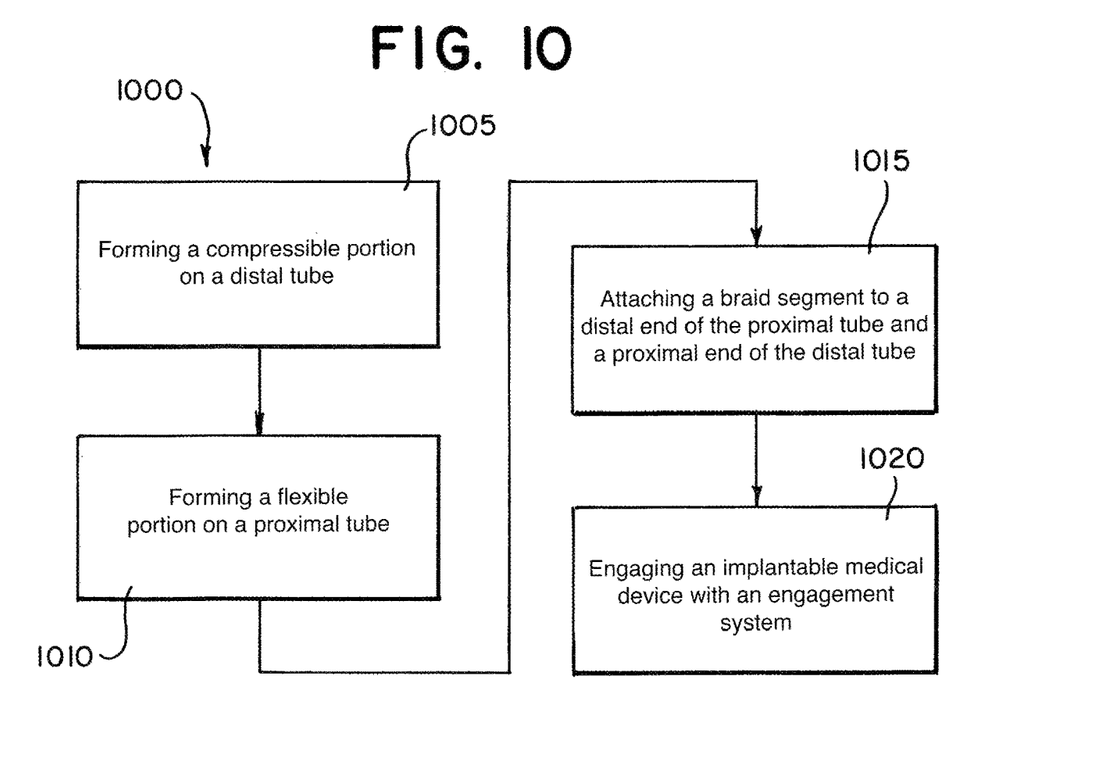
FIG. 10 is a flow diagram outlining the steps of detaching an implantable medical device, according to aspects of the present invention.

FIG. 10 is a flow diagram illustrating a method 1000 of detaching an implantable medical device. The implantable medical device can include a device 12, 612 such as illustrated and describe herein, a variation thereof, or alternative thereto as understood by a person skilled in the art according to the teachings herein. The method can include one or more of the following steps presented in no particular order. The example method 1000 can include additional steps as appreciated and understood by a person of ordinary skill in the art. The example method can be performed by an example detachment system 10 as disclosed herein, a variation thereof, or an alternative thereto as appreciated and understood by a person of ordinary skill in the art.

In step 1005, a compressible portion 306 on a distal tube 300 can be formed. The compressible portion 306 on a distal tube 300 can be formed by spiral-cutting a portion of the distal tube 300.

In step 1010, a flexible portion 106 on a proximal tube 100 can be formed. The flexible portion 106 on the proximal tube 100 can be formed by interference cuts along at least a portion of the proximal tube 100.

In step 1015 a braid segment 200a, 200b, 200c can be attached to a distal end 104 of the proximal tube 100 and a proximal end 302 of the distal tube 300.

In step 1020, the implantable medical device 12 can be engaged with an engagement system 140, 400. The engagement system 140, 400 can include a locking member 140 and a loop wire 400.

The method can include using the loop wire 400 with the locking member 140 to engage the implantable medical device 12 and applying force to the loop wire 400 to move the compressible portion 306 to the compressed condition.

The method can include wrapping the braid segment 200b around a polymer liner 204 prior to attaching the braid segment 200b to the distal end 104 of the proximal tube 100 and the proximal end of the distal tube 300.

The method can include sliding a polymer sleeve 206 over the proximal tube 100, the braid segment 200c and at least a portion of the distal tube 300. The polymer sleeve 206 can be engaged to the implantable medical device.

The method can include engaging the polymer sleeve 206 to the implantable medical device 12.

The method can include coating the polymer sleeve 206 with one or more hydrophilic coating 208.

During detachment, the method can include applying a force on the locking member 140; disengaging the implantable medical device 12; and allowing the compressible portion 306 to return to the elongated condition. By moving the compressible portion 306 to the elongated condition, the implantable medical device 12 can be deployed.

The descriptions contained herein are examples of embodiments of the invention and are not intended in any way to limit the scope of the invention. As described herein, the invention contemplates many variations and modifications of the inventive delivery and release system for a vascular occlusion device, including numerous configurations, numerous stiffness properties and methods for delivering the same. Also, there are many possible variations in the materials and configurations of the release mechanism. These modifications would be apparent to those having ordinary skill in the art to which this invention relates and are intended to be within the scope of the claims which follow.

What is claimed is:

1. A detachment system for delivering an implantable medical device to a target location of a body vessel (BV), comprising:
   a generally hollow, relatively stiff proximal tube having a proximal end and a distal end, the distal end comprising a flexible section;
   a generally hollow, relatively flexible distal tube comprising:
      a proximal end;

a distal end; and
a compressible portion of the relatively flexible distal tube itself which is axially movable from a compressed condition to an elongated condition;
a flexible braid segment disposed between the proximal end of the relatively flexible distal tube and the flexible section of the distal end of the relatively stiff proximal tube, the flexible braid segment formed from a plurality of wires;
a polymer sleeve disposed over at least a portion of the flexible section of the relatively stiff proximal tube, the entirety of the braid segment, and the entirety of the relatively flexible distal tube; and
an engagement system configured to engage and deploy the implantable medical device disposed at the distal end of the distal tube; wherein the polymer sleeve is fixedly attached to the relatively flexible distal tube or the relatively stiff proximal tube.

2. The detachment system of claim 1, wherein the flexible braid segment is concentrically disposed around a polymer liner.

3. The detachment system of claim 1, wherein the polymer sleeve includes one or more hydrophilic coatings.

4. The detachment system of claim 1, wherein the polymer sleeve has a wall having a thickness of between approximately 0.02 millimeters and approximately 0.08 millimeters.

5. The detachment system of claim 1, wherein the flexible braid segment includes between approximately 8 and approximately 16 wires.

6. The detachment system of claim 1, wherein the plurality of wires have a pick per inch of between approximately 50 and approximately 100.

7. The detachment system of claim 1, wherein the compressible portion of the relatively flexible distal tube is a spiral-cut portion of the relatively flexible distal tube.

8. The detachment system of claim 1, wherein the flexible section of the distal end of the relatively stiff proximal tube comprises a spiral-cut portion.

9. The detachment system of claim 1, wherein the engagement system is configured to:
move the compressible portion to the compressed condition when engaging the implantable medical device; and
deploy the implantable medical device when releasing the compressible portion to the elongated condition.

10. The detachment system of claim 1, wherein the compressible portion is adapted to automatically move to the elongated condition when the engagement system is disengaged from the implantable medical device.

11. A method of detaching an implantable medical device, comprising
forming a compressible portion on a proximal end of a relatively flexible distal tube;
forming a flexible portion on a distal end of a relatively stiff proximal tube;
attaching a flexible braid assembly to the distal end of the relatively stiff proximal tube and the proximal end of the relatively flexible distal tube;
sliding a polymer sleeve over at least a portion of the flexible section of the relatively stiff proximal tube, the entirety of the flexible braid assembly, and the entirety of the relatively flexible distal tube; fixedly attaching the polymer sleeve to the relatively flexible distal tube or the relatively stiff proximal tube; and
engaging the implantable medical device with an engagement system.

12. The detachment method of claim 11, further comprising engaging the polymer sleeve to the implantable medical device.

13. The detachment method of claim 11, further comprising coating the polymer sleeve with one or more hydrophilic coating.

14. The detachment method of claim 11, further comprising wrapping the flexible braid assembly around a polymer liner prior to attaching the flexible braid assembly to the distal end of the relatively stiff proximal tube and the proximal end of the relatively flexible distal tube.

15. The detachment method of claim 11, wherein the engagement system comprises a locking member, and a loop wire,
wherein engaging the implantable medical device with the engagement system further comprises using the loop wire with the locking member to engage the implantable medical device; and
applying force to the loop wire to move the compressible portion to a compressed condition.

16. The detachment method of claim 15, further comprising:
applying a force on the locking member;
disengaging the implantable medical device; and
allowing the compressible portion to return to an elongated condition.

17. The detachment method of claim 11, wherein forming the compressible portion on the relatively flexible distal tube includes spiral-cutting a portion of the relatively flexible distal tube.

18. The detachment method of claim 11, further comprising deploying the implantable medical device by moving the compressible portion to an elongated condition.

* * * * *